United States Patent [19]

Hayashi et al.

[11] Patent Number: 5,571,918
[45] Date of Patent: Nov. 5, 1996

[54] METHOD FOR PRODUCING 2-METHYLSPIRO(1,3-OXATHIOLANE-5,3')QUINUCLIDINE

[75] Inventors: Koji Hayashi; Sho Tokumoto; Hiroshi Yoshizawa; Tatsuo Isogai; Masaru Kimura; Masahiko Sawaki; Takayoshi Ando, all of Yokkaichi; Isamu Katsuyama, Kasugai; Hayato Ariyoshi; Tadashi Nakamura, both of Yokkaichi, all of Japan

[73] Assignee: Ishihara Sangyo Kaisha Ltd., Osaka, Japan

[21] Appl. No.: 439,576

[22] Filed: May 11, 1995

[30] Foreign Application Priority Data

| May 19, 1994 | [JP] | Japan | 6-130907 |
| Jun. 10, 1994 | [JP] | Japan | 6-152873 |
| Sep. 27, 1994 | [JP] | Japan | 6-258802 |
| Mar. 20, 1995 | [JP] | Japan | 7-087461 |

[51] Int. Cl.$^6$ .................................................. C07D 453/02
[52] U.S. Cl. ........................................................... 546/18
[58] Field of Search ................................................. 546/18

[56] References Cited

U.S. PATENT DOCUMENTS 4,861,886  8/1989  Haga et al. .............................. 546/16

FOREIGN PATENT DOCUMENTS 0205247  12/1986  European Pat. Off. .
0303391   2/1989  European Pat. Off. .

*Primary Examiner*—John M. Ford
*Attorney, Agent, or Firm*—Oblon, Spivak, McClelland, Maier & Neustadt, P.C.

[57] ABSTRACT

A method for producing 2-methylspiro(1,3-oxathiolane-5,3')quinuclidine, which comprises reacting 3-hydroxy-3-mercaptomethylquinuclidine or a salt thereof and a carbonyl compound in the presence of a catalyst made of at least one member selected from the group consisting of tin halides, oxyacids of phosphorus, phosphorus oxyhalides and organic sulfonic acids, to produce cis-form 2-methylspiro(1,3-oxathiolane-5,3')quinuclidine or a salt thereof.

16 Claims, No Drawings

METHOD FOR PRODUCING 2-METHYLSPIRO(1,3-OXATHIOLANE-5,3')QUINUCLIDINE

The present invention relates to a method for industrially advantageously producing cis-form 2-methylspiro(1,3-oxathiolane-5,3')quinuclidine (hereinafter referred to simply as C-MSOQ) or a salt thereof useful for the treatment of diseases of the central nervous system in mammals, particularly for the treatment of diseases due to disturbances of central cholinargic function and autoimmune diseases which are so-called Sjoegren syndrome, or its intermediate. Particularly, the present invention relates to a method for producing C-MSOQ, and more particularly to a method for directly producing C-MSOQ by reacting 3-hydroxy-3-mercaptomethylquinuclidine (hereinafter referred to simply as QHT) or a salt thereof and a carbonyl compound in the presence of a certain specific catalyst, or a method for producing C-MSOQ or a salt thereof by firstly producing a mixture of trans-form and cis-form MSOQ or salts thereof and then isomerizing the trans-form 2-methylspiro(1,3-oxathiolane-5,3')quinuclidine (hereinafter referred to simply as T-MSOQ) or a salt thereof in the presence of a certain specific catalyst to C-MSOQ or a salt thereof.

2-Methylspiro(1,3-oxathiolane-5,3')quinuclidine (hereinafter referred to simply as MSOQ) can be produced by condensing QHT and acetaldehyde in the presence of a boron trifluoride-ethyl ether complex catalyst, as disclosed in e.g. published European Patent Application No. 0205247 and Japanese Unexamined Patent Publication No. 280497/1986. However, MSOQ as such a reaction product is usually obtained in the form of a mixture of geometrical isomers i.e. T-MSOQ (the one wherein the methyl group at the 2-position and the nitrogen atom at the 1'-position are located on the opposite sides of the plane of the 1,3-oxathiolane ring) and C-MSOQ (the one wherein the methyl group at the 2-position and the nitrogen atom at the 1'-position are located on the same side of the plane of the 1,3-oxathiolane ring. Then, C-MSOQ is isolated from the mixture of T-MSOQ and C-MSOQ as the above-mentioned reaction product by e.g. fractional crystallization.

Further, U.S. Pat. No. 4,861,886 and Japanese Unexamined Patent Publications No. 16787/1989, No. 45387/1989 and No. 104079/1989 disclose methods wherein T-MSOQ is isomerized to C-MSOQ in the presence of a Lewis acid of a metal halide, sulfuric acid or an organic sulfonic acid as a catalyst.

By the above conventional methods, the productivity of C-MSOQ can be improved to some extent. However, an industrially advantageous method has still been desired which is capable of further improving the productivity and reducing the production costs of C-MSOQ. For example, in each of the conventional methods, it is desired to simplify the reaction process steps and reduce the loads in the purification and separation steps by producing a large amount of C-MSOQ directly from QHT and acetaldehyde. Or, in the case where a mixture of T-MSOQ and C-MSOQ is firstly produced from QHT and acetaldehyde, it is desired to produce a large amount of C-MSOQ and to reduce the loads in the purification and separation steps by using a catalyst which is easy to handle and readily available on an industrial scale, or by using an isomerization catalyst having a higher catalytic activity, as compared with the conventional boron trifluoride.ethyl ether complex catalyst.

The present inventors have conducted detailed studies on each step of the condensation reaction and the isomerization reaction and as a result, have surprisingly found that when a certain specific catalyst is present in the condensation reaction of QHT and acetaldehyde, rich C-MSOQ can be produced directly, and when QHT and acetaldehyde are reacted for condensation in the presence of a certain catalyst, a mixture of T-MSOQ and C-MSOQ is excellently produced, and when this mixture is reacted in the presence of a catalyst made of a tin halide, if necessary together with a certain cocatalyst, rich C-MSOQ can be produced. According to such methods of the present invention, a reaction product rich in C-MSOQ can be obtained in good yield, whereby purification and separation of C-MSOQ from the reaction product are easy, and the separation yield is high. Further, the catalysts used have no particular problems with respect to the availability and handling efficiency for an industrial operation. Furthermore, the reaction process can be simplified and the loads in the purification and separation steps can be reduced. Thus, the productivity of C-MSOQ can be remarkably improved.

It is an object of the present invention to provide a method for producing MSOQ industrially advantageously.

Another object of the present invention is to provide a method for industrially advantageously producing a reaction product of MSOQ rich in C-MSOQ.

According to the first aspect, the present invention provides a method for producing MSOQ, which comprises reacting QHT or a salt thereof and a carbonyl compound in the presence of a catalyst made of at least one member selected from the group consisting of tin halides, oxyacids of phosphorus, phosphorus oxyhalides and organic sulfonic acids, to produce C-MSOQ or a salt thereof.

According to the second aspect, the present invention provides a method for producing MSOQ, which comprises isomerizing T-MSOQ or acid addition salts thereof in the presence of a catalyst of a tin halide to produce C-MSOQ or a salt thereof.

According to the third aspect, the present invention provides a method for producing MSOQ, which comprises condensing QHT or a salt thereof and a carbonyl compound in the presence of at least one member selected from the group consisting of hydrogen chloride, sulfuric acid and an organic sulfonic acid, to produce a mixture of T-MSOQ and C-MSOQ or salts thereof.

Further, according to the fourth aspect, the present invention provides a method for producing MSOQ, which comprises subjecting the mixture of T-MSOQ and C-MSOQ or salts thereof obtained by the condensation of QHT or a salt thereof and the carbonyl compound, to the above-mentioned isomerization reaction to produce C-MSOQ or a salt thereof.

In the present invention, QHT as the starting material, C-MSOQ, or a mixture of T-MSOQ and C-MSOQ, as the reaction product, includes salts thereof, such as salts thereof with inorganic acids or organic acids. Further, in the present invention, QHT, T-MSOQ, C-MSOQ or acid addition salts thereof include the respective racemic modifications and optical isomers of (d) and (e). When they are used as starting materials or intermediates for the above-mentioned reactions of the present invention, it is possible to produce the corresponding racemic modifications or optical isomers.

Now, the first aspect of the present invention will be described.

The carbonyl compound to be used in the first aspect of the present invention may be acetaldehyde, acetal or paraacetaldehyde. Among them, acetaldehyde is preferred.

The starting material QHT can be produced by various methods. For example, it can readily be produced by reacting spiro(oxylane-2,3')quinuclidine with hydrogen sulfide, as disclosed in e.g. the above-mentioned published European Patent Application No. 0205247 or Japanese Unexamined Patent Publication No. 280497/1986, or by a method similar thereto.

The catalyst to be used in the first aspect of the present invention is at least one member selected from the group consisting of tin halides, oxyacids of phosphorus, phosphorus oxyhalides and organic sulfonic acids. Specific examples of the catalyst component include stannic halides such as stannic chloride and stannic bromide; oxyacids of phosphorus such as phosphoric acid, phosphorus oxyhalides such as phosphorus oxychloride and phosphorus oxybromide; and organic sulfonic acids such as benzene sulfonic acid, o, m or p-toluenesulfonic acid, methanesulfonic acid, trifluoromethanesulfonic acid and anhydrides thereof. However, from the viewpoint of the ratio of T-MSOQ/C-MSOQ in the reaction product, the reaction yield, etc., a stannic halide, phosphoric acid, phosphorus oxychloride or p-toluenesulfonic acid is preferred. More preferred is stannic chloride or stannic bromide. Most preferred is stannic chloride. The amount of the catalyst component to be used, varies depending upon the types of the carbonyl compound and the solvent, the method for preparation of the catalyst, the reaction temperature, etc., and it can not be generally defined. However, it is usually from 1 to 5 mols, preferably from 2 to 3 mols, per mol of the starting material QHT or a salt thereof.

In the reaction of QHT and the carbonyl compound, a solvent is usually employed. As such a solvent, any type may be employed so long as it is inert to the reaction. For example, at least one member selected from the group consisting of halogenated hydrocarbons such as chloroform, methylene chloride and 1,2-dichloroethane; aromatic hydrocarbons such as benzene, toluene and xylene; and aprotic polar solvents such as dimethylsulfoxide and dimethylformamide, may be employed. Preferred is at least one member selected from the group consisting of chloroform, methylene chloride, 1,2-dichloroethane, toluene and dimethylsulfoxide. Among them, chloroform is particularly preferred. The amount of the solvent can not generally be defined for the same reason as in the case of the amount of the above-mentioned catalyst component. However, it is usually from 500 to 10,000 parts by weight, preferably from 500 to 2,000 parts by weight, per mol of the starting material QHT or a salt thereof.

The amounts of QHT or a salt thereof and the carbonyl compound in the method of this invention can not generally be defined, since they vary depending upon the types of the carbonyl compound, the catalyst and the solvent, the reaction conditions, etc. However, it is usual to use from 1 to 10 mols, preferably from 2 to 5 mols, of the carbonyl compound per mol of QHT or a salt thereof.

In the method of the first aspect of this invention, a predetermined amount of the carbonyl compound is added to a solution having QHT or a salt thereof dissolved or dispersed in a solvent, and then a predetermined amount of the catalyst is added. Then, the reaction is carried out usually at a temperature of from −15° to +50° C., preferably from 0° to 20° C., for from 1 to 48 hours. If necessary, the reaction is conducted in a nitrogen atmosphere while supplying a nitrogen gas during the reaction. The reaction product containing MSOQ thus obtained is purified by washing, extraction or treatment with an aqueous sodium hydroxide solution, chloroform or sulfuric acid. Purified MSOQ may be extracted with a solvent such as n-hexane and obtained as an oily substance. However, it is also possible to supply hydrogen chloride gas or to add an isopropyl alcohol solution of hydrogen chloride, to the extract solution of MSOQ to convert it to an acid addition salt such as MSOQ hydrochloride and to obtain stable crystals. MSOQ composed of a mixture of trans-form and cis-form isomers thus obtained has the ratio of C-MSOQ to T-MSOQ increased, for example, to a level of at least 60/40 (weight ratio). Accordingly, it is readily possible to separate C-MSOQ or a salt thereof from such a mixture of trans-form and cis-form isomers by various methods such as column chromatography, fractional crystallization or their combination.

By the method according to the first aspect of the present invention, a reaction product containing a large amount of C-MSOQ or a salt thereof can be obtained directly from QHT or a salt thereof and a carbonyl compound, as compared with the conventional method disclosed in e.g. the above-mentioned published European Patent Application No. 0205247, whereby it is possible to reduce the loads in the process steps for purifying and separating C-MSOQ or a salt thereof from the reaction product. In addition to such a merit, it is unnecessary to conduct two steps for the condensation reaction of QHT or a salt thereof and a carbonyl compound and the isomerization reaction separately, as required in the method disclosed in e.g. the above-mentioned U.S. Pat. No. 4,861,886.

Now, other aspects of the present invention will be described.

Here, at least one member selected from the group consisting of hydrogen chloride, sulfuric acid and an organic sulfonic acid is used as a catalyst when QHT or a salt thereof and the carbonyl compound are condensed to produce MSOQ. At that time, the reaction can be carried out by incorporating the catalyst to a solution having QHT or a salt thereof and the carbonyl compound as the starting materials preliminarily dissolved in a solvent or by incorporating the catalyst at the same time as the addition of the starting materials. The manner of incorporation is suitably selected taking into consideration, the starting materials, handling efficiency of the catalyst, the reaction operation, etc. The types and preferred embodiments of the carbonyl compound and the organic sulfonic acid to be used here may be the same or substantially the same as used for the above-mentioned method according to the first aspect of the invention. The hydrogen chloride is preferably hydrogen chloride containing substantially no moisture, and hydrogen chloride gas is more preferred from the industrial point of view. On the other hand, the sulfuric acid is preferably highly concentrated sulfuric acid, and from the industrial point of view, concentrated sulfuric acid, particularly the one having a concentration of at least 95%, is preferred. In the condensation reaction, in addition to the above catalyst, a dehydrating agent may preferably be incorporated, so that the rate of reaction between QHT and the carbonyl compound can further be improved. Various dehydrating materials may be used as the dehydrating agent. Specifically, inorganic salts, inorganic oxides and their anhydrides or partially dehydrated products thereof may, for example, be mentioned. As such a dehydrating agent, at least one member selected from the group consisting of sodium sulfate, sodium hydrogen sulfate, calcium chloride, calcium sulfate, magnesium chloride, magnesium sulfate, zeolite, alumina, silica, and their anhydrides and partially dehydrated products, is preferred from the viewpoint of economical availability and handling efficiency. Among them, sodium sulfate, calcium chloride or zeolite is particularly preferred.

The amounts of QHT or a salt thereof and the carbonyl compound used here as the starting materials may be the same or substantially the same as in the above-mentioned method according to the first aspect of the present invention.

The amount of the hydrogen chloride or the organic sulfonic acid used as the catalyst, can not generally be defined, since it varies depending upon the types of the carbonyl compound and the solvent, the reaction conditions, the reactor, etc. However, it is usually from 1 to 8 mols, preferably from 2 to 5 mols, per mol of the starting material QHT or a salt thereof. Likewise, the amount of sulfuric acid can not generally be defined as in the case of the hydrogen chloride, but it is usually from 0.5 to 4 mols, preferably from 1.0 to 3 mols, per mol of QHT or a salt thereof. Likewise, the amount of the dehydrating agent can not generally be defined, but it is usually from 0.01 to 5 parts by weight, preferably from 0.05 to 3 parts by weight, per part by weight of QHT or a salt thereof.

In the condensation reaction of QHT or a salt thereof and the carbonyl compound, a solvent is usually employed. Specific examples and preferred examples of such a solvent as well as the amount may be the same or substantially the same as in the case of the first aspect of the present invention.

In carrying out the condensation reaction of QHT or a salt thereof and the carbonyl compound, mixing of starting materials such as QHT or a salt thereof, the carbonyl compound, the solvent, the catalyst and the dehydration agent, and the order of their addition may suitably be selected taking into consideration the handling efficiency of these materials, the reaction operation, the reactor, etc. Usually, a predetermined amount of the carbonyl compound is added to a solution having QHT or a salt thereof dissolved or dispersed in a solvent, and then after adding a predetermined amount of the catalyst, or after adding the dehydrating agent, followed by an addition of such a catalyst, the reaction is carried out usually at a temperature of from $-15°$ to $+50°$ C., preferably from $0°$ to $30°$ C., for from 1 to 48 hours. When hydrogen chloride gas is used as the catalyst, the starting materials are dissolved in a solvent, and if necessary, a dehydrating agent is added to the solution, and then the reaction is carried out by directly blowing the hydrogen chloride gas into the solution. Further, by conducting the reaction, in a nitrogen atmosphere while supplying nitrogen gas during the reaction, it is possible to prevent a side reaction. The reaction mixture containing MSOQ thus obtained can be purified by extraction or back extraction with e.g. an aqueous sodium hydroxide solution, chloroform or sulfuric acid. Usually, MSOQ is finally extracted with a solvent such as n-hexane in the form of an oily substance, and by supplying hydrogen chloride gas or by adding an iso-propyl alcohol solution containing hydrogen chloride, to such an extract solution, it is possible to convert it to an acid addition salt such as MSOQ hydrochloride and to obtain it in the form of stable crystals. MSOQ thus obtained is usually in the form of a mixture of T-MSOQ and C-MSOQ or salts thereof.

In the condensation reaction process of QHT or a salt thereof and the carbonyl compound in the present invention, a catalyst which is easy to handle and readily available on an industrial scale, is used, as compared with the conventional method disclosed in e.g. the above-mentioned published European Patent Application No. 0205248. Namely, the boron trifluoride-ethyl ether complex catalyst used in the conventional method is highly volatile and is not easy to handle, and not only that, it requires special treating operations for corrosion prevention of reactor and for waste water treatment. Besides, such a catalyst is expensive and hardly constantly available. Whereas, the above-mentioned catalyst used in the condensation reaction method of the present invention has no such drawbacks.

Further, this mixture of T-MSOQ and C-MSOQ or salts thereof is subjected to a reaction of isomerizing T-MSOQ or acid addition salts thereof to C-MSOQ in the presence of a catalyst of a tin halide, to obtain a reaction product rich in C-MSOQ or a salt thereof. As the acid addition salts of T-MSOQ, addition salts of T-MSOQ with various inorganic acids or organic acids may be used. Specific examples of the acids constituting them include inorganic acids such as hydrochloric acid, phosphoric acid, sulfuric acid, hydrobromic acid, hydroiodic acid and sulfumic acid; and organic acids such as benzenesulfonic acid, p-toluenesulfonic acid, acetic acid, lactic acid, succinic acid, maleic acid, tartaric acid, citric acid, gluconic acid, ascorbic acid, benzoic acid and cinnamic acid.

The tin halide catalyst used here may be the same or substantially the same as those types and preferred embodiments of the tin halides used in the method according to the first aspect of the invention. However, as specific examples, stannic halides such as stannic chloride, stannic bromide and their mixtures may be mentioned.

Further, when an inorganic acid, an organic acid, an alcohol or a mixture thereof is used as a cocatalyst together with such a tin halide catalyst, the isomerization reaction can further be accelerated. Various types of inorganic acids and organic acids may be used as the cocatalyst. Specific examples include inorganic acids such as hydrogen chloride, sulfuric acid and phosphoric acid; and organic acids such as methanesulfonic acid, ethanesulfonic acid, vinylsulfonic acid, acetylenesulfonic acid, trifluoromethanesulfonic acid, benzenesulfonic acid, p-toluenesulfonic acid, p-chlorobenzenesulfonic acid, dodecylbenzenesulfonic acid and naphthalenesulfonic acid. Further, as the alcohol, various types may likewise be used. As a specific example, a lower alkyl alcohol may be mentioned. Preferably, methyl alcohol, ethyl alcohol, or n- or iso-propyl alcohol may be used.

With respect to such a catalyst, from the viewpoint of e.g. the reactivity for isomerization and the reaction yield, a stannic halide is preferred as the tin halide. Particularly preferred is stannic chloride. Further, as the above-mentioned cocatalyst, preferred is at least one member selected from the group consisting of hydrogen chloride, sulfuric acid, phosphoric acid, benzenesulfonic acid, p-toluenesulfonic acid, methyl alcohol, ethyl alcohol and n- and iso-propyl alcohols. Among them, hydrogen chloride or ethyl alcohol is particularly preferred. More preferably, stannic chloride is used as the above tin halide catalyst, and hydrogen chloride and ethyl alcohol are used in combination as the cocatalyst. The above hydrogen chloride is preferably the one having a water content of less than a certain level, and anhydrous hydrogen chloride is more preferred.

The amount of the above tin halide catalyst component can not generally be defined, since it varies depending upon the types of the acid addition salt of T-MSOQ, the catalyst, the cocatalyst and the solvent, the reaction conditions, the reactor, etc. However, the tin halide catalyst is used usually in an amount of from 1 to 5 mols, preferably from 1 to 3 mols, per mol of T-MSOQ or acid addition salts thereof. Likewise, the amount of the cocatalyst component can not generally be defined. However, in the case of an alcohol, the amount is usually from 0.1 to 2 mols, preferably from 0.3 to 1.2 mols, per mol of T-MSOQ or acid addition salts thereof. Further, in the case of an inorganic acid or an organic acid, the amount is usually from 0.1 to 5 mols, preferably from 0.1 to 1 mol. Further, the acid concentration of the inorganic acid or the organic acid as a cocatalyst can not generally be defined, since it varies depending upon the type of the acid and other reaction conditions. However, such an acid can be used in various concentrations. In a case where the acid catalyst is not only effective as a catalyst component but also forms an acid addition salt with T-MSOQ, it will be necessary to incorporate it additionally in an amount required for forming the salt in addition to the amount as the solvent.

In this isomerization reaction step, a solvent is usually employed. Specific examples and preferred examples of such a solvent may be the same or substantially the same as in the method according to the first aspect of the present invention. Any solvent may be employed so long as it is inert to the reaction. The amount of the solvent can not generally be defined, but the solvent is usually used in an amount of from 20 to 60 parts by weight per part by weight of the starting material T-MSOQ. Further, in connection with the above solvent, when an alcohol (such as ethyl alcohol) is contained as a stabilizing agent as in the case of chloroform, it is necessary to additionally incorporate it in an amount required as a cocatalyst for the above isomerization reaction in addition to the amount used as a solvent.

In this isomerization reaction step, mixing of starting materials such as T-MSOQ or acid addition salts thereof, the solvent, the catalyst and the cocatalyst, and the order of their addition may suitably be selected taking into consideration handling efficiency of these materials, the reaction operation, the reactor, etc. Usually, a predetermined amount of a tin halide catalyst, or such a tin halide catalyst and an inorganic acid or an organic acid as a cocatalyst, are added to a solution having T-MSOQ or acid addition salts thereof dissolved or dispersed in a solvent containing an alcohol as a cocatalyst for the isomerization reaction, and then the isomerization reaction is carried out usually at a temperature of from −15° to +50° C., preferably from 0° to 20° C., for from 1 to 48 hours. When the isomerization reaction is carried out, the tin halide or the cocatalyst may be introduced all at once, or may be introduced in a divided fashion. Further, acid addition salts of T-MSOQ may be the acid addition salts preliminarily produced. Further, in a case where hydrogen chloride is used as a cocatalyst, hydrogen chloride gas may be blown into the reaction solution. Further, in the reaction system, T-MSOQ and an acid component, or an acid component as a cocatalyst, may be reacted to form an acid addition salt of T-MSOQ, and then the isomerization reaction may be carried out. Further, this isomerization reaction may be carried out in a nitrogen atmosphere while supplying nitrogen gas.

After completion of the isomerization reaction, the reaction product thus obtained is subjected to post treatment in accordance with a conventional method. For example, the reaction product is purified by suitable washing, extraction or treatment with water, an aqueous sodium hydroxide solution, chloroform or sulfuric acid. Purified MSOQ is extracted with a solvent such as n-hexane and obtained as an oily substance. In order to obtain further stable crystals, it may be converted to and taken out in the form of an acid addition salt of MSOQ. As the acid addition salts of MSOQ, various salts of inorganic acids or organic acids may be mentioned, as mentioned above. For example, when MSOQ is to be converted to MSOQ hydrochloride, hydrogen chloride gas may be supplied, or an isopropyl alcohol solution containing hydrochloric acid may be added to the above-mentioned extract solution of MSOQ as an oily substance, for conversion to the hydrochloride of MSOQ. Further, when it is to be converted to a phosphate of MSOQ, an aqueous phosphoric acid solution and a solution containing an alcohol such as methyl alcohol or ethyl alcohol may be added to the above-mentioned extract solution of MSOQ as an oily substance, to convert it to a phosphate of MSOQ.

T-MSOQ or its acid addition salt to be used in this isomerization step is not limited to any specific concentration of T-MSOQ, and the one having any concentration may be employed. For example, it may be composed solely of T-MSOQ or its acid addition salt, or it may be the one containing a small amount or a large amount of C-MSOQ in addition to T-MSOQ. By subjecting T-MSOQ or its acid addition salt alone or a mixture thereof with C-MSOQ or its salt to such an isomerization step, at least 40%, preferably at least 50%, of T-MSOQ or its acid addition salt can be isomerized to C-MSOQ to obtain a product rich in C-MSOQ. C-MSOQ or its acid addition salt purified and taken out as described above, can readily be isolated by column chromatography, fractional crystallization or a combination thereof, or by various other methods.

By the above-mentioned isomerization step of the present invention, a large amount of C-MSOQ can be produced by the isomerization reaction of T-MSOQ or its acid addition salt, as compared with the conventional methods disclosed in the above-mentioned published European Patent Application No. 0205247 and U.S. Pat. No. 4,861,886. Particularly, in the latter prior art, it is disclosed to use a Lewis acid of a metal halide, sulfuric acid or an organic sulfonic acid as an isomerization reaction catalyst, but there is no specific description with respect to a catalyst of a tin halide used in the present invention. Besides, according to the present invention, a large amount of C-MSOQ or a salt thereof can be produced as compared with the catalyst disclosed in the prior art. Thus, according to the present invention, not only the yield of C-MSOQ can be improved in the isomerization step, but also it is possible to reduce the loads in the purification and separation steps of C-MSOQ from the reaction product.

Now, the present invention will be described in further detail with reference to Examples. However, it should be understood that the present invention is by no means restricted by such specific Examples.

EXAMPLE 1

Into a 200 ml four-necked flask equipped with a stirrer, a thermometer and a calcium chloride tube, 3.46 g of 3-hydroxy-3-mercaptomethylquinuclidine (QHT) and 149.2 g of chloroform were charged and cooled to 4° C. with ice water. Then, 3.96 g of acetaldehyde was added thereto. While maintaining the temperature at a level of from 5° to 10° C., 15.63 g of stannic chloride was dropwise added thereto over a period of about 30 minutes. Then, mixture was maintained at room temperature for 24 hours with stirring.

To a white slurry-like reaction product, 50 g of water was introduced, and the product was dissolved. Then, 27 g of a 48% sodium hydroxide aqueous solution was dropwise added to convert the solution to strongly alkaline. The lower chloroform layer was separated, and 10 g of chloroform was added to the remaining aqueous layer for re-extraction. Then, to this chloroform layer, 23.4 g of 5% sulfuric acid was added for conversion to a sulfate, which was then extracted to water. Then, the solution was again made alkaline with 12.7 g of a 10% sodium hydroxide aqueous solution to free the desired product, which was then extracted four times with 8 g of n-hexane. The extract n-hexane layer was dried over anhydrous sodium sulfate, and then sodium sulfate was removed by filtration to obtain a hexane solution of 2-methylspiro(1,3-oxathiolane-5, 3')quinuclidine (MSOQ).

To this hexane solution, 3.6 g of a 15% hydrochloric acid/iso-propyl alcohol solution was dropwise added to obtain MSOQ hydrochloride. The precipitated white crystals were collected by filtration to obtain 3.67 g of a mixture of hydrochlorides of the cis-form and transform MSOQ (yield to QHT: 78%). The ratio of the cis-form to the trans-form of this mixture was analyzed by liquid chromatography, whereby C-MSOQ/T-MSOQ=91/9 (weight ratio).

EXAMPLE 2

Into a 200 ml four-necked flask as used in Example 1, 3.46 g of QHT and 74.5 g of chloroform were charged and cooled to 4° C. with ice water. Then, 2.64 g of acetaldehyde was added thereto. While maintaining the mixture at a temperature of from 5° to 10° C., 13.8 g of phosphorus oxychloride was dropwise added over a period of about 30 minutes. Then, the mixture was maintained at room temperature for 24 hours with stirring.

Post treatment was carried out in the same manner as in Example 1 to obtain 2.0 g of MSOQ hydrochloride (yield to QHT: 42.5%). The C-MSOQ/T-MSOQ ratio of this product was 65/35 (weight ratio).

EXAMPLE 3

Into a 200 ml four-necked flask as used in Example 1, 3.46 g of QHT and 74.5 g of chloroform were charged and cooled to a temperature of from 10° to 15° C. with ice water. Then, 2.64 g of acetaldehyde was added thereto. While maintaining the temperature at the same level, 4.41 g of 99% phosphoric acid was introduced thereto, and then the mixture was maintained at room temperature for 24 hours with stirring.

Post treatment was carried out in the same manner as in Example 1 to obtain 1.4 g of MSOQ hydrochloride (yield to QHT: 29.7%). The C-MSOQ/T-MSOQ ratio of this product was 72/28 (weight ratio).

EXAMPLE 4

Into a 200 ml four-necked flask as used in Example 1, 3.46 g of QHT and 74.5 g of chloroform were charged and cooled to a temperature of from 10° to 15° C. with ice water. Then, 2.64 g of acetaldehyde was added thereto. While maintaining the temperature at the same level, 7.74 g of p-toluenesulfonic anhydride was introduced thereto, and then the mixture was maintained at room temperature for 24 hours with stirring.

Post treatment was carried out in the same manner as in Example 1 to obtain 3.1 g of MSOQ hydrochloride (yield to QHT: 65.8%). The C-MSOQ/T-MSOQ ratio of this product was 67/33 (weight ratio).

COMPARATIVE EXAMPLE 1

Into a 200 ml four-necked flask as used in Example 1, 3.46 g of QHT and 74.5 g of chloroform were charged and cooled to a temperature of from 0° to 5° C. with ice water. Then, 2.64 g of acetaldehyde was added thereto. While maintaining the temperature at a level of from 5° to 10° C., 12.8 g of a boron trifluoride-ethyl ether complex compound was dropwise added thereto. Then, the mixture was maintained at room temperature for two hours with stirring.

Post treatment was carried out in the same manner as in Example 1 to obtain 1.75 g of MSOQ hydrochloride (yield to QHT: 37.1%). The C-MSOQ/T-MSOQ ratio of this product was 58/42 (weight ratio).

EXAMPLE 5

(1) Into a 500 ml four-necked flask equipped with a stirrer, a thermometer and a calcium chloride tube, 10.6 g of QHT (purity: 98.3%), 222.8 g of chloroform, 31.7 g of toluene and 2.2 g of dimethylsulfoxide were charged, and 17.3 g of acetaldehyde was added thereto at a temperature of from 10° to 15° C. while cooling with ice water. While maintaining the temperature at the same level, 12.2 g of anhydrous sodium sulfate was added thereto. Then, 9.8 g of hydrogen chloride gas was blown thereinto over a period of two hours, and then the mixture was maintained at room temperature for 6 hours with stirring.

To the reaction mixture, 125.7 g of a 15% sodium hydroxide aqueous solution was dropwise added to make the reaction mixture strongly alkaline. Then, undissolved inorganic salts were separated by filtration, and the inorganic salts were washed with 18.9 g of chloroform. The filtrate was subjected to liquid separation, and the aqueous layer was re-extracted with chloroform. These chloroform layers were put together, and 100.5 g of 5% sulfuric acid was added thereto to obtain desired MSOQ sulfate. Then, it was again made alkaline with 54.6 g of a 10% sodium hydroxide aqueous solution to free the desired MSOQ, which was then extracted four times with 33 g of n-hexane. The n-hexane layer was dried over anhydrous sodium sulfate, and then, sodium sulfate was filtered off to obtain a n-hexane solution of MSOQ. To this n-hexane solution, 18.0 g of an iso-propyl alcohol solution containing 20% of hydrochloric acid was dropwise added to obtain MSOQ hydrochloride. After stirring for 3 hours, precipitated white crystals were collected by filtration to obtain 10.1 g of a mixture of hydrochlorides of T-MSOQ and C-MSOQ (purity: 95.8%, yield of pure product to QHT: 68.5%).

(2) Into a 500 ml four-necked flask equipped with a stirrer and a thermometer, 4.9 g (0.02 mol) of the mixture of hydrochlorides of T-MSOQ and C-MSOQ obtained in the above step (1) (the weight ratio of C-MSOQ/T-MSOQ was 50.5/49.5) and 34 ml of chloroform (this chloroform contained 0.5 wt % of ethyl alcohol) were charged, and 17 ml of a chloroform solution containing 0.2 g of hydrogen chloride (this chloroform also contained 0.5 wt % of ethyl alcohol) was added thereto with stirring. Then, 7.8 g of stannic chloride was dropwise added thereto over a period of 30 minutes, and an isomerization reaction was carried out with stirring at room temperature for 24 hours.

To the reaction product, 50 ml of water was added, and a 48% sodium hydroxide aqueous solution was added thereto with stirring to make the reaction mixture strongly alkaline. Then, the chloroform layer was separated. To the aqueous solution, 10 ml of chloroform was added for re-extraction. These chloroform layers were put together, and 24.0 g of 5% sulfuric acid was added thereto to convert MSOQ in the reaction mixture to a sulfate, which was then dissolved in water. To this aqueous layer, a 10% sodium hydroxide aqueous solution was again added to make it strongly alkaline and to free MSOQ in the reaction mixture. Then, it was extracted four times with 15 ml of n-hexane. The extracted n-hexane layer was dried over anhydrous sodium sulfate. Then, an iso-propyl alcohol solution containing 20% of hydrochloric acid was dropwise added thereto to convert MSOQ in the reaction mixture to a hydrochloride, and precipitated white crystals were collected by filtration and dried to obtain 4.4 g of a mixture containing hydrochlorides of C-MSOQ and T-MSOQ (yield to the starting material mixture of MSOQ hydrochlorides: 92.1%). With respect to this mixture, the ratio of C-MSOQ to T-MSOQ was analyzed by liquid chromatography, whereby C-MSOQ/T-MSOQ was 98.6/1.4 (weight ratio).

EXAMPLE 6

Into a 500 ml four-necked flask as used in Example 5(1), 18.5 g of QHT (purity: 93.3%), 260.0 g of chloroform, 37.0 g of toluene and 2.6 g of dimethylsulfoxide were charged, and 19.8 g of acetaldehyde was added thereto at a temperature of from 10° to 15° C. while cooling with ice water. While maintaining the temperature at the same level, 18.0 g of molecular sieve 3A was added thereto, and then 9.4 g of hydrogen chloride gas was blown thereinto over a period of two hours. Then, the mixture was maintained at room temperature for 17.5 hours with stirring.

To the reaction mixture, 209.5 g of a 15% sodium hydroxide aqueous solution was dropwise added to make the reaction mixture strongly alkaline. Then, molecular sieve 3A was filtered off, and molecular sieve 3A was washed with 31.5 g of chloroform. The filtrate was subjected to liquid separation. The aqueous layer was again extracted with chloroform. These chloroform layers were put together, and 165.5 g of 5% sulfuric acid was added thereto to convert the desired MSOQ to a sulfate. Then, it was again made alkaline with 91.0 g of a 10% sodium hydroxide aqueous solution to free the desired MSOQ, which was then extracted four times with 55.0 g of n-hexane. The n-hexane layer was dried over anhydrous sodium sulfate, and sodium sulfate was filtered off to obtain a n-hexane solution of MSOQ. To this n-hexane solution, 23.2 g of an iso-propyl alcohol solution containing 20% of hydrochloric acid was dropwise added to obtain a hydrochloride of MSOQ, and precipitated white crystals were collected by filtration to obtain 16.0 g of a mixture of hydrochlorides of T-MSOQ and C-MSOQ (purity: 95.1%, yield of the pure product to QHT: 64.6%). With respect to this mixture, the ratio of C-MSOQ to T-MSOQ was analyzed by liquid chromatography, whereby C-MSOQ/T-MSOQ was 50.0/50.0 (weight ratio).

EXAMPLE 7

Into a 500 ml four-necked flask as used in Example (1), 10.6 g of QHT (purity: 98.3%), 222.8 g of chloroform, 31.7 g of toluene and 2.2 g of dimethylsulfoxide were charged, and 17.3 g of acetaldehyde was added thereto at a temperature of from 10° to 15° C. while cooling with ice water. While maintaining the temperature at the same level, 9.8 g of hydrogen chloride gas was blown thereinto over a period of two hours. Then, the mixture was maintained at room temperature for 18 hours with stirring.

To the reaction mixture, 125.7 g of a 15% sodium hydroxide aqueous solution was dropwise added to make the reaction mixture strongly alkaline, and the solution was subjected to liquid separation to obtain a chloroform layer. The aqueous layer was re-extracted with 57.2 g of chloroform. These chloroform layers were put together, and 100.5 g of 5% sulfuric acid was added thereto to obtain desired MSOQ sulfate. Then, it was again made alkaline with 54.6 g of a 10% sodium hydroxide aqueous solution to free the desired MSOQ, which was then extracted four times with 33.0 g of n-hexane. The n-hexane layer was dried over anhydrous sodium sulfate. Then, sodium sulfate was filtered off to obtain a n-hexane solution of MSOQ. To this n-hexane solution, 17.0 g of an iso-propyl alcohol solution containing 20% of hydrochloric acid was dropwise added to obtain MSOQ hydrochloride, and precipitated white crystals were collected by filtration to obtain 9.3 g of a mixture of hydrochlorides of T-MSOQ and C-MSOQ (purity: 94.7%, yield of the pure product to QHT: 62.3%). With respect to this mixture, the ratio of C-MSOQ to T-MSOQ was analyzed by liquid chromatography, whereby C-MSOQ/T-MSOQ was 50.0/50.0 (weight ratio).

EXAMPLE 8

Into a 500 ml four-necked flask as used in Example 5(1), 9.0 g of QHT (purity: 95.7%), 130.0 g of chloroform, 18.5 g of toluene and 1.3 g of dimethylsulfoxide were charged, and 9.9 g of acetaldehyde was added thereto at a temperature of from 10° to 15° C. while cooling with ice water. While maintaining the temperature at the same level, 15.0 g of 98% concentrated sulfuric acid was dropwise added thereto over a period of two hours. Then, the mixture was maintained at room temperature for 18 hours with stirring.

To the reaction mixture, 90.0 g of a 15% sodium hydroxide aqueous solution was dropwise added to make the reaction mixture strongly alkaline. Then, undissolved inorganic salts were filtered off, and the inorganic salts were washed with 33.0 g of chloroform. The filtrate was subjected to liquid separation. The aqueous layer was re-extracted with chloroform. These chloroform layers were put together, and 67.0 g of 5% sulfuric acid was added thereto to obtain desired MSOQ sulfate. Then, it was again made alkaline with 38.0 g of a 10% sodium hydroxide aqueous solution to free the desired MSOQ, which was then extracted four times with 19.0 g of n-hexane. The n-hexane layer was dried over anhydrous sodium sulfate. Then, sodium sulfate was filtered off to obtain a n-hexane solution of MSOQ. To this n-hexane solution, 17.0 g of an iso-propyl alcohol solution containing 20% of hydrochloric acid was dropwise added to obtain MSOQ hydrochloride, and precipitated white crystals were collected by filtration to obtain 7.0 g of a mixture of hydrochlorides of T-MSOQ and C-MSOQ (purity: 93.7%, yield of the pure product to QHT: 55.7%). With respect to this mixture, the ratio of C-MSOQ to T-MSOQ was analyzed by liquid chromatography, whereby C-MSOQ/T-MSOQ was 51.7/48.3 (weight ratio).

COMPARATIVE EXAMPLE 2

Into a 500 ml four-necked flask as used in Example 5(1), 10.6 g of QHT (purity: 98.3%), 222.8 g of chloroform, 31.7 g of toluene and 2.2 g of dimethylsulfoxide were charged, and 17.3 g of acetaldehyde was added thereto at a temperature of from 10° to 15° C. while cooling with ice water. While maintaining the temperature at the same level, 37.5 g of $BF_3$ ethyl ether was dropwise added thereto over a period of two hours. Then, the mixture was maintained at room temperature for two hours with stirring.

Post treatment was carried out in the same manner as in Example 5(1), to obtain 10.5 g of a mixture of hydrochlorides of T-MSOQ and C-MSOQ (purity: 94.1%, yield of the pure product to QHT: 70.0%). With respect to this mixture, the ratio of C-MSOQ to T-MSOQ was analyzed by liquid chromatography, whereby C-MSOQ/T-MSOQ was 60.3/39.7 (weight ratio).

EXAMPLE 9

Into a 500 ml four-necked flask equipped with a stirrer, a thermometer and a calcium chloride tube, 450 g of a chloroform solution of QHT (corresponding to 0.158 mol of QHT) was charged, and 31.3 g of acetaldehyde was added thereto at a temperature of from 10° to 15° C. while cooling with ice water. While maintaining the temperature at the same level, 22.4 g of anhydrous sodium sulfate was added thereto. Then, 31.0 g of 98% concentrated sulfuric acid was dropwise added thereto over a period of 30 minutes. Then, the mixture was maintained at room temperature for 20 hours with stirring.

To the reaction mixture, 253 g of a 15% sodium hydroxide aqueous solution was dropwise added to make the reaction mixture strongly alkaline. Then, precipitated inorganic salts were collected by filtration, and the inorganic salts were washed with 50.0 g of chloroform. The filtrate was subjected to liquid separation, and the aqueous layer was re-extracted with chloroform. These chloroform layers were put together, and 188 g of 5% sulfuric acid was added thereto to obtain desired MSOQ sulfate. Then, it was again made alkaline with 102 g of a 10% sodium hydroxide aqueous solution to free the desired MSOQ, which was then extracted four times with 61.0 g of n-hexane. The n-hexane solution was dried over anhydrous sodium sulfate, and then sodium sulfate was filtered off to obtain a n-hexane solution of MSOQ. To this n-hexane solution, 23.0 g of an iso-propyl alcohol solution containing 20% of hydrochloric acid was dropwise added to obtain MSOQ hydrochloride, and precipitated white crystals were collected by filtration to obtain 22.3 g of a mixture of hydrochlorides of T-MSOQ and C-MSOQ (yield: 60.0%). With respect to this mixture, the ratio of C-MSOQ to T-MSOQ was analyzed by liquid chromatography, whereby C-MSOQ/T-MSOQ was 50.0/50.0 (weight ratio).

COMPARATIVE EXAMPLE 3

Into a 500 ml four-necked flask as used in Example 9, 285 g of a chloroform solution of QHT (corresponding to 0.1 mol of QHT) was charged, and 19.8 g of acetaldehyde was added thereto at a temperature of from 10° to 15° C. while cooling with ice water. While maintaining the temperature at the same level, 42.5 g of $BF_3$.ethyl ether was dropwise added thereto over a period of 30 minutes. Then, the mixture was maintained at room temperature for 3 hours with stirring.

To the reaction mixture, 147 g of a 15% sodium hydroxide aqueous solution was dropwise added to make the reaction mixture strongly alkaline. Then, precipitated inorganic salts were filtered off, and the inorganic salts were washed with 22.0 g of chloroform. The filtrate was subjected to liquid separation, and the aqueous layer was re-extracted with chloroform. These chloroform layers were put together, and 117 g of 5% sulfuric acid was added to obtain desired MSOQ sulfate. Then, it was again made alkaline with 64.0 g of a 10% sodium hydroxide aqueous solution to free the desired MSOQ, which was then extracted four times with 38.0 g of n-hexane. The n-hexane layer was dried over anhydrous sodium sulfate. Then, sodium sulfate was filtered off to obtain a n-hexane solution of MSOQ. To this n-hexane solution, 14.0 g of an iso-propyl alcohol containing 20% of hydrochloric acid was dropwise added to obtain MSOQ hydrochloride, and precipitated white crystals were collected by filtration to obtain 14.4 g of a mixture of hydrochlorides of T-MSOQ and C-MSOQ (yield: 61.2%). With respect to this mixture, the ratio of C-MSOQ to T-MSOQ was analyzed by liquid chromatography, whereby C-MSOQ/T-MSOQ was 61.5/38.5 (weight ratio).

EXAMPLE 10

Into a 300 ml four-necked flask equipped with a stirrer and a thermometer, 4.7 g (0.02 mol) of starting material MSOQ hydrochloride (weight ratio of C-MSOQ/T-MSOQ was 0.7/99.3) and 100 ml of chloroform were charged, and 7.8 g (0.03 mol) of stannic chloride was dropwise added thereto over a period of 5 minutes with stirring. Further, 0.15 g of concentrated sulfuric acid was added thereto, and an isomerization reaction was carried out while stirring the mixture at room temperature for 24 hours.

To a white slurry-like reaction product, 50 ml of water was added, and a 48% sodium hydroxide aqueous solution was added thereto with stirring to make the reaction product strongly alkaline. Then, the chloroform layer was separated. The aqueous layer was re-extracted with 10 ml of chloroform. The chloroform layers were put together, and 33 g of 3.5% sulfuric acid was added thereto to convert MSOQ in the reaction mixture to a sulfate, which was then dissolved in water. This aqueous layer was again made strongly alkaline by an addition of a 10% sodium hydroxide aqueous solution to free MSOQ in the reaction mixture. Then, it was extracted four times with 15 ml of n-hexane. The extract n-hexane layer was dried over anhydrous sodium sulfate, and an iso-propyl alcohol solution containing 16% of hydrochloric acid was dropwise added thereto to convert MSOQ in the reaction mixture to a hydrochloride, and precipitated white crystals were collected by filtration and dried to obtain 4.03 g of a mixture comprising hydrochlorides of C-MSOQ and T-MSOQ (yield to starting material MSOQ: 85.7%, the same applies hereinafter). With respect to this mixture, the ratio of C-MSOQ to T-MSOQ was analyzed by liquid chromatography, whereby C-MSOQ/T-MSOQ was 97/3 (weight ratio).

EXAMPLE 11

The reaction was carried out in the same manner as in Example 10 except that stannic chloride was changed to 15.63 g (0.06 mol), concentrated sulfuric acid was changed to 1 g and the reaction time was changed to 5 hours, and post treatment of the reaction product was carried out to obtain 3.82 g of MSOQ hydrochloride comprising C-MSOQ and T-MSOQ (yield: 81.3%). The C-MSOQ/T-MSOQ ratio of this product was 94/6 (weight ratio).

EXAMPLE 12

The reaction was carried out in the same manner as in Example 10 except that the solvent was changed to methylene chloride, and post treatment of the reaction product was carried out to obtain 4.06 g of MSOQ hydrochloride comprising C-MSOQ and T-MSOQ (yield: 86.4%). The C-MSOQ/T-MSOQ ratio of this product was 95/5 (weight ratio).

EXAMPLE 13

Into a 300 ml four-necked flask as used in Example 10, 3.4 g (0.012 mol) of starting material of MSOQ phosphate (the weight ratio of C-MSOQ/T-MSOQ was 9/91) and 100 ml of chloroform were charged, and 4.2 g (0.016 mol) of stannic chloride was dropwise added thereto over a period of 5 minutes under stirring. The isomerization reaction was carried out while stirring the mixture at room temperature for 20 hours.

Then, in the same manner as in Example 10, post treatment of the reaction product was carried out to obtain 2.02 g of MSOQ hydrochloride comprising C-MSOQ and T-MSOQ (yield: 71.3%). The C-MSOQ/T-MSOQ ratio of this product was 87/13 (weight ratio).

EXAMPLE 14

The reaction was carried out in the same manner as in Example 10 except that starting material MSOQ phosphate (the weight ratio of C-MSOQ/T-MSOQ was 9/91) was used in an amount of 5.94 g (0.02 mol), and post treatment of the reaction product was carried out to obtain 3.39 g of MSOQ hydrochloride comprising C-MSOQ and T-MSOQ (yield: 72.1%). The C-MSOQ/T-MSOQ ratio of this product was 96/4 (weight ratio).

COMPARATIVE EXAMPLE 4

The reaction was carried out in the same manner as in Example 10 except that no stannic chloride was added although 1 g of concentrated sulfuric acid was added. The C-MSOQ/T-MSOQ ratio in the reaction system after 24 hours was 20/80 (weight ratio).

EXAMPLE 15

Into a 1 l four-necked flask equipped with a stirrer and a thermometer, 23.55 g (0.1 mol) of starting material MSOQ hydrochloride (the weight ratio of C-MSOQ/T-MSOQ was 60.4/39.6) and 250 ml (1 mol per T-MSOQ) of chloroform (containing 0.5 wt % of ethyl alcohol, the same applies in the following Examples 16 and 17), were charged. Then, 39.08 g (0.15 mol) of stannic chloride was dropwise added thereto over a period of 30 minutes with stirring, and the isomerization reaction was carried out while stirring at room temperature for 24 hours. To a white slurry-like reaction product, 250 ml of water was added, and a 48% sodium hydroxide aqueous solution was added thereto with stirring to make the reaction mixture strongly alkaline. Then, the chloroform layer was separated. The aqueous layer was re-extracted by an addition of 50 ml of chloroform. These chloroform layers were put together, and 117 g of 5% sulfuric acid was added thereto to convert MSOQ in the reaction mixture to a sulfate which was then dissolved in water. This aqueous layer was again made strongly alkaline by an addition of a 10% sodium hydroxide aqueous solution to free MSOQ in the reaction mixture. Then, it was extracted four times with 75 ml of n-hexane. The extract n-hexane layer was dried over anhydrous sodium sulfate, and then an iso-propyl alcohol solution containing 16% of hydrochloric acid was dropwise added thereto to convert C-MSOQ in the reaction mixture to a hydrochloride. Precipitated white crystals were collected by filtration and dried to obtain 22.3 g of a mixture comprising hydrochlorides of C-MSOQ and T-MSOQ (yield to starting material MSOQ: 94.8%, the same applies hereinafter). With respect to this mixture, the ratio of C-MSOQ to T-MSOQ was analyzed by liquid chromatography, whereby C-MSOQ/T-MSOQ was 98.2/1.8 (weight ratio).

EXAMPLE 16

Into a 3 l four-necked flask equipped with a stirrer and a thermometer, 70.65 g (0.3 mol) of starting material MSOQ hydrochloride (the weight ratio of C-MSOQ/T-MSOQ was 56.8/43.2) and 550 ml of chloroform were charged, and a solution containing 2.2 g of hydrochloric acid (calculated as hydrogen chloride) and 200 ml of chloroform (1 mol of total ethyl alcohol per T-MSOQ, 0.2 mol of HCl per T-MSOQ) were added thereto with stirring. Then, 117.2 g (0.45 mol) of stannic chloride was dropwise added thereto over a period of 30 minutes, and the mixture was reacted at room temperature for 24 hours.

Post treatment was carried out in the same manner as in Example 15 to obtain 66.14 g of MSOQ hydrochloride comprising C-MSOQ and T-MSOQ (yield: 93.6%). The C-MSOQ/T-MSOQ ratio of this product was 98.7/1.3 (weight ratio).

EXAMPLE 17

Into a 100 l GL reactor, 3,768 g (16 mols) of starting material MSOQ hydrochloride (the weight ratio of C-MSOQ/T-MSOQ was 6.6/93.4) and 49.3 kg of chloroform were charged, and a solution containing 0.12 kg (calculated as hydrogen chloride) of hydrochloric acid and 10.8 kg of chloroform (0.5 mol of total ethyl alcohol per T-MSOQ, 0.21 mol of HCl per T-MSOQ) were added thereto with stirring. Then, 3,908 g of stannic chloride was dropwise added thereto over a period of 40 minutes, and the mixture was reacted at a temperature of from 25° to 30° C. for 20 hours. The C-MSOQ/T-MSOQ ratio of this reaction product was 98.7/1.3 (weight ratio), and the amount was 3,617 g (yield: 96%).

EXAMPLE 18

Into a 100 ml four-necked flask equipped with a stirrer and a thermometer, 4.7 g (0.02 mol) of starting material MSOQ hydrochloride (the weight ratio of C-MSOQ/T-MSOQ was 56.8/43.2) and 50 ml of methylene chloride were charged, and 7.8 g (0.03 mol) of stannic chloride was dropwise added thereto over a period of 10 minutes with stirring. The mixture was reacted at room temperature for 24 hours. The C-MSOQ/T-MSOQ ratio of this reaction product was 88.3/11.7 (weight ratio). Further, to this reaction product, 0.3 g of ethyl alcohol in methylene chloride (0.8 mol per T-MSOQ) was added, followed by the same reaction, whereby the C-MSOQ/T-MSOQ ratio of the reaction product was 97.1/2.9 (weight ratio), and the amount was 4.25 g (yield: 90.5%).

EXAMPLE 19

The reaction was carried out in the same manner as in Example 18 except that the solvent was changed to 1,2-dichloroethane, whereby the C-MSOQ/T-MSOQ ratio of this reaction product was 90.1/9.9 (weight ratio). Further, to this reaction product, ethyl alcohol was added, followed by the same reaction, whereby the C-MSOQ/T-MSOQ ratio of this reaction product was 97.1/2.9 (weight ratio), and the amount was 4.28 (yield: 91%).

EXAMPLE 20

(1) Into a four-necked flask equipped with a stirrer, a thermometer, a calcium chloride tube and a gas supply tube, 13.9 g (0.1 mol) of spiro(oxylane-2,3')quinuclidine (hereinafter referred to simply as QE), 260.0 g of chloroform, 31.7 g of toluene and 1.72 g of p-toluenesulfonic anhydride were charged. Then, while blowing hydrogen sulfide gas thereinto at a rate of 18.6 ml per minute at room temperature with stirring, the reaction was carried out for 6 hours, whereupon the peak of QE disappeared as the reaction was monitored by gas chromatography, and a mixed solution of QHT in chloroform and toluene was obtained.

(2) Into a 500 ml four-necked flask equipped with a stirrer, a thermometer and a calcium chloride tube, the mixed solution obtained in the above step (1) was charged, and 19.8 g of acetaldehyde was added thereto at a temperature of from 10° to 15° C. while cooling with ice water. While maintaining the temperature at the same level, 14.2 g of anhydrous sodium sulfate was introduced thereto. Then, 98% concentrated sulfuric acid was dropwise added thereto over a period of 30 minutes, and then the mixture was maintained at room temperature for 5 hours with stirring.

To the reaction mixture, 209.5 g of a 15% sodium hydroxide aqueous solution was dropwise added to make the reaction mixture strongly alkaline. Then, undissolved inorganic salts were separated by filtration, and the inorganic salts were washed with 31.5 g of chloroform. The filtrate was subjected to liquid separation. The aqueous layer was re-extracted with chloroform. The chloroform layers were put together, and 165.5 g of 5% sulfuric acid was added thereto to obtain desired MSOQ sulfate. Then, it was again made alkaline with 91.0 g of a 10% sodium hydroxide aqueous solution to free the desired MSOQ, which was then extracted four times with 55 g of n-hexane. The n-hexane layer was dried over anhydrous sodium sulfate. Then, sodium sulfate was filtered off to obtain a n-hexane solution of MSOQ. To this n-hexane solution, 32.4 g of an iso-propyl alcohol solution containing 20% of hydrochloric acid was dropwise added to obtain MSOQ hydrochloride. After stirring for 3 hours, precipitated white crystals were collected by filtration to obtain 18.3 g of a mixture of hydrochlorides of T-MSOQ and C-MSOQ (purity: 95.0%, yield of the pure product to QE: 73.8%, the weight ratio of C-MSOQ/T-MSOQ was 60.0/40.0).

(3) Into a 500 ml four-necked flask equipped with a stirrer and a thermometer, 4.9 g (0.02 mol) of the mixture of T-MSOQ and C-MSOQ obtained in the above step (2) and 34 ml of chloroform (this chloroform contained 0.5 wt % of ethyl alcohol) were charged, and 17 ml of a chloroform solution containing 0.2 g of hydrogen chloride (this chloroform also contained 0.5 wt % of ethyl alcohol) was added thereto with stirring. Then, 7.8 g of stannic chloride was dropwise added thereto over a period of 30 minutes, and the isomerization reaction was carried out at room temperature for 24 hours with stirring.

To the reaction product, 50 ml of water was added, and a 48% sodium hydroxide aqueous solution was added with stirring to make the reaction mixture strongly alkaline. Then, the chloroform layer was separated. The aqueous layer was re-extracted by an addition of 10 ml of chloroform. These chloroform layers were put together, and 24.0 g of 5% sulfuric acid was added thereto to convert MSOQ in the reaction mixture to a sulfate, which was then dissolved in water. To this aqueous layer, a 10% sodium hydroxide aqueous solution was again added to make it strongly alkaline to free MSOQ in the reaction mixture. Then, the freed MSOQ was extracted four times with 15 ml of n-hexane. The extract n-hexane layer was dried over anhydrous sodium sulfate, and then an iso-propyl alcohol solution containing 20% of hydrochloric acid, was dropwise added to convert MSOQ in the reaction mixture to a hydrochloride, and precipitated white crystals were collected by filtration and dried to obtain 4.4 g of a mixture comprising hydrochlorides of C-MSOQ and T-MSOQ. With respect to this mixture, the ratio of C-MSOQ to T-MSOQ was analyzed by liquid chromatography, whereby C-MSOQ/T-MSOQ was 98.5/1.5 (weight ratio).

In the present invention, C-MSOQ or a salt thereof can be produced directly by reacting QHT or a salt thereof and a carbonyl compound in the presence of a certain specific catalyst, or it is possible to condense these starting materials in the presence of a certain catalyst to produce a mixture of T-MSOQ and C-MSOQ or salts thereof and then isomerize this mixture to C-MSOQ in the presence of a certain specific catalyst to obtain C-MSOQ or a salt thereof. By such methods, the reaction product contains a high proportion of C-MSOQ. Accordingly, it is possible to obtain a large amount of C-MSOQ or a salt thereof, or to reduce the loads in the steps of separating and purifying C-MSOQ from the reaction product. Accordingly, according to the present invention, it is possible to industrially advantageously produce C-MSOQ which is useful for the treatment of diseases of the central nervous system in mammals, particularly for the treatment of diseases due to disturbances of central cholinargic function and autoimmune diseases which are so-called Sjoegren syndrome.

We claim:
1. A method for producing 2-methylspiro(1,3-oxathiolane- 5,3')quinuclidine, which comprises reacting 3-hydroxy-3-mercaptomethylquinuclidine or a salt thereof and a carbonyl compound in the presence of a catalyst made of at least one member selected from the group consisting of tin halides, oxyacids of phosphorus, phosphorus oxyhalides and organic sulfonic acids, to produce cis-form 2-methylspiro(1, 3-oxathiolane-5,3')quinuclidine or a salt thereof.

2. The method according to claim 1, wherein the catalyst is a stannic halide, phosphoric acid, phosphorus oxychloride, p-toluenesulfonic acid or a mixture thereof.

3. The method according to claim 1, wherein the reaction is carried out at a reaction temperature of from −15° to +50° C. in the presence of from 1 to 5 mols of the catalyst per mol of 3-hydroxy-3-mercaptomethylquinuclidine.

4. A method for producing 2-methylspiro(1,3-oxathiolane- 5,3')quinuclidine, which comprises isomerizing trans-form 2-methylspiro(1,3-oxathiolane-5,3')quinuclidine or acid addition salts thereof in the presence of a catalyst of a tin halide, to produce cis-form 2-methylspiro( 1,3-oxathiolane-5,3')quinuclidine or a salt thereof.

5. The method according to claim 4, wherein the isomerization is carried out in the presence of a cocatalyst made of at least one member selected from the group consisting of inorganic acids, organic acids and alcohols.

6. The method according to claim 5, wherein the cocatalyst is made of at least one member selected from the group consisting of hydrogen chloride, sulfuric acid, phosphoric acid, benzene sulfonic acid, p-toluenesulfonic acid, methyl alcohol, ethyl alcohol, and n- and iso-propyl alcohols.

7. The method according to claim 5, the isomerization is carried out in the presence of hydrogen chloride and ethyl alcohol as the cocatalyst.

8. The method according to claim 5, wherein the isomerization is carried out at a reaction temperature of from −15° to +50° C. in the presence of from 1 to 5 mols of the catalyst of a tin halide and from 0.1 to 5 mols of the cocatalyst, per mol of the trans-form 2-methylspiro( 1,3-oxathiolane-5, 3')quinuclidine or acid addition salts thereof.

9. The method according to claim 4, wherein 3-hydroxy-3-mercaptomethylquinuclindine or a salt thereof and a carbonyl compound are condensed in the presence of at least one member selected from the group consisting of hydrogen chloride, sulfuric acid and an organic sulfonic acid, to produce a mixture of trans-form and cis-form 2-methylspiro(1,3-oxathiolane-5,3')quinuclidines or salts thereof, and this mixture is subjected to the above isomerization to produce cis-form 2-methylspiro( 1,3-oxathiolane-5,3')quinuclidine or a salt thereof.

10. A method for producing 2-methylspiro(1,3-oxathiolane- 5,3'-quinuclidine, which comprises condensing 3-hydroxy- 3-mercaptomethylquinuclidine or a salt thereof and a carbonyl compound in the presence of at least one member selected from the group consisting of hydrogen chloride, sulfuric acid and an organic sulfonic acid, to produce a mixture of trans-form and cis-form 2-methyspiro( 1,3-oxathiolane-5,3')quinuclidines or salts thereof.

11. The method according to claim 9 or 10, wherein the condensation is carried out in the presence of a dehydrating agent.

12. The method according to claim 11, wherein the dehydrating agent is at least one member selected from the group consisting of sodium sulfate, sodium hydrogen-sulfate, calcium chloride, calcium sulfate, magnesium chloride, magnesium sulfate, zeolite, alumina, silica, and anhydrides and partially dehydrated products thereof.

13. The method according to claim 10, wherein the condensation is carried out at a reaction temperature of from −15° to +50° C. in the presence of from 1 to 8 mols of hydrogen chloride, from 0.5 to 4 mols of sulfuric acid or from 1 to 8 mols of an organic sulfonic acid, per mol of 3-hydroxy-3-mercaptomethylquinuclidine or a salt thereof, and in the presence of from 0.01 to 5 parts by weight of a dehydrating agent per part by weight of the 3-hydroxy-3-mercaptomethylquinuclidine or a salt thereof.

14. The method according to claim 1, 9 or 10, wherein the carbonyl compound is acetaldehyde.

15. The method according to claim 1, 4 or 9, wherein the catalyst is stannic chloride.

16. The method according to claim 1, 4 or 10, wherein the reaction is carried out in the presence of a solvent.

* * * * *